United States Patent [19]

Whitehead

[11] Patent Number: 4,765,837
[45] Date of Patent: Aug. 23, 1988

[54] ALLOY AND PRODUCT MADE THEREFROM

[76] Inventor: Derek J. Whitehead, Poynton, Cheshire, England

[21] Appl. No.: 9,540

[22] Filed: Feb. 2, 1987

[30] Foreign Application Priority Data

Feb. 4, 1986 [GB] United Kingdom ............. 8602679

[51] Int. Cl.[4] ............................................. B22F 3/00
[52] U.S. Cl. ...................................... 75/249; 419/66; 420/408; 420/411
[58] Field of Search .................. 420/408, 411; 75/249; 419/66

[56] References Cited

U.S. PATENT DOCUMENTS

| 1,975,375 | 10/1934 | Schichtel | 420/411 |
| 2,546,931 | 3/1951 | Leman et al. | 420/411 |
| 3,291,656 | 12/1966 | Mann | 420/408 |
| 4,040,129 | 8/1977 | Steinemann et al. | 420/419 |
| 4,600,661 | 7/1986 | Dohnomoto et al. | 420/408 |

FOREIGN PATENT DOCUMENTS

| 470538 | 5/1972 | Australia . |
| 673067 | 11/1965 | Belgium . |
| 1560365 | 12/1967 | France . |
| 1030101 | 2/1965 | United Kingdom . |
| 1172673 | 12/1966 | United Kingdom . |

OTHER PUBLICATIONS

Chem. Abstracts, 100: 208274B (1974).

Primary Examiner—Stephen J. Lechert, Jr.
Attorney, Agent, or Firm—Donald Brown; Ernest V. Linek

[57] ABSTRACT

A pellet or bolus for administration to a ruminant by deposition in its rumeno-reticular sac where it is eroded away by rumen juices and releases active agent(s) and-/or components, either continuously or in pulsed doses, comprises or incorporates a magnesium-based alloy which comprises at least 40% of magnesium, at least 30% zinc and up to 20% aluminium and, optionally, copper up to 5%, and trace elements, selected from cobalt, manganese, nickel and selenium up to 1%, the percentages being by weight. A paste can be made by heating the alloy to between its solidus and liquidus points, when it can be admixed with lead shot for weighting the bolus.

In the illustrated case, the bolus comprises tubular sheath 14 which contains alloy/iron shot filling 16. However, the alloy can be used for any appropriate component of the bolus.

21 Claims, 2 Drawing Sheets

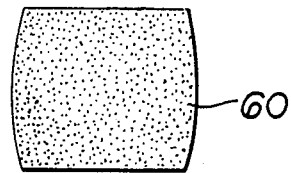
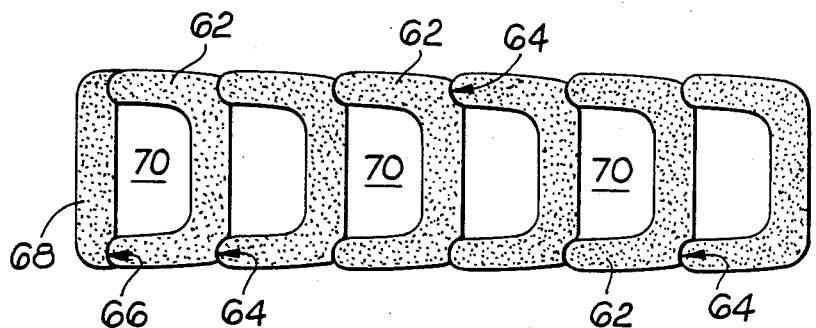
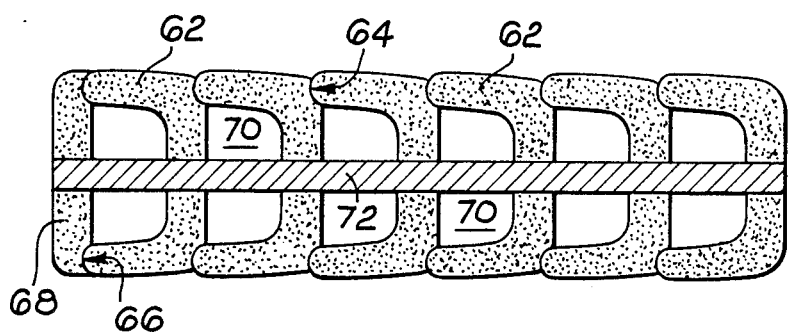

ALLOY AND PRODUCT MADE THEREFROM

BACKGROUND OF THE INVENTION

This invention concerns a novel alloy of which the constituents, or the principal constituents, are magnesium, zinc and aluminium, said alloy being particularly suitable for use in the production of, or incorporation into, products in the form of pellets containing magnesium and other metallic, animal-dietary supplements or active agents for administering to ruminants by deposition into the rumeno-reticular sac, for example by means of an oesophageal balling gun, where they dissolve in the rumen juices, e.g., over a period of several weeks, to provide a continuous or dosed supply of magnesium with or without other valuable metallic elements and/or active agents for assimilation by the animal. The invention further concerns products in the form of pellets as aforesaid.

The specification of British Patent No. 1 030 101 teaches that pellets for administration to ruminants should have a preferred minimum density of 2.25 gm/ml to avoid shedding by the animal, and proposes a suitable alloy containing at least 75% magnesium and having a preferred aluminium content of 8 to 15%. These percentages are by weight and wherever percentages are recited in this specification, they are all given by weight. The density of such alloys is approximately 1.8 gm/ml and to achieve a pellet with a density in excess of 2.25 gm/ml it is necessary to weight the pellet by incorporating a dense insoluble material, such as iron shot. A commercially-available pellet has heretofore been manufactured from a magnesium-based alloy containing 12% aluminium and 2% copper weighted by reason of approximately 50% of the overall weight of the pellet being of fine iron shot. Such pellets have a density of approximately 2.8 gm/ml and have been widely used for the protection of cattle and sheep from hypomagnesaemia.

The known pellets are difficult to manufacture due to the wide difference between the density of the magnesium alloy (1.8 gm/ml) and that of the iron (7.3 gm/ml). A usual method of fabrication utilises the wide freezing range of the magnesium alloy. The alloy is heated to an elevated temperature between its liquidus and solidus points and the required quantity of iron shot is mixed with the resultant pasty alloy. The pasty mixture, at the elevated temperature, is introduced into open mould cavities and pressed to the required shape. Difficulties are experienced with such manufacturing processes, arising from segregation of the iron shot and the aluminium-rich eutectic constituent of the magnesium alloy. It is also necessary to avoid alloying of the surfaces of the iron shot particles if the corrosion rate of the pellets is not to be adversely affected.

SUMMARY OF THE INVENTION

According to the present invention we provide an alloy of which the constituents, or the principal constituents, are magnesium, zinc and aluminium, and suitable for use in the production of, or incorporation in a pellet for administration to a ruminant by deposition into its rumeno-reticular sac, characterised in that said alloy comprises magnesium to the extent of at least 40%, zinc at least 30%, and aluminium up to 20%.

The alloy may contain other elements, e.g., copper up to 5%. A preferred composition is as follows:

Magnesium from 45% to 50%
Zinc from 34% to 42%
Aluminium from 5% to 15%
Copper from 0% to 5%

In general, pellets made from such alloys have inherently high densities, e.g., from 2.5 to 2.9 gm/ml, so that it is not indispensible to weight them with iron shot or other high density materials. The alloys have good castability and are readily fabricated into pellets by gravity diecasting or pressure diecasting techniques. The use of special manufacturing processes such as have heretofore been necessary with iron shot-loaded pellets are hence no longer essential, although it is, of course, possible for the alloy of the invention to be used in conjunction with iron shot, if so desired. Moreover, although the main purpose of the zinc content is to increase the density of the alloy, it is also beneficial to ruminants when assimilated.

The aluminium and copper content of the alloy are instrumental in controlling corrosion characteristics, castability and mechanical properties of cast pellets. Thus, a magnesium-zinc binary alloy containing 50% of zinc is hard and brittle when diecast and unsuitable for pellet manufacture. The presence of 5% to 15% of aluminium and up to 5% of copper reduces this brittleness and improves castability. The presence of the copper, in amounts up to 5%, improves corrosion characteristics and is of value in alleviating deficiency diseases other than hypomagnesaemia.

Similarly, additional elements such as cobalt, manganese, nickel, and selenium, or combinations thereof may be present, in quantities up to 1%, to provide trace element sources. Moreover, by increasing the proportion of cobalt and nickel the corrosion rate of the alloy may be increased; manganese has the effect of reducing the corrosion rate of the alloy.

As has already been indicated, the densities of pellets made from, containing, or incorporating alloys according to this invention are generally high enough to avoid shedding when administered to cattle and sheep. Nevertheless, in cases where higher densities are required, such may be achieved by incorporating iron shot, or similar dense inert matter, in the alloy. The low melting point and low tendency to oxidation of the molten alloy made this particularly easy. For example, by mixing three parts by weight of S170 grade iron shot with one part by weight of magnesium alloy containing 38% zinc, 11% aluminium and 2% copper and heating the mixture to an elevated temperature between the solidus and liquidus points of the alloy, a pasty mixture having a density of 5 gm/ml is obtained. Other alloys within the compositional range 45% to 50% magnesium, 30% to 40% zinc, 5% to 15% aluminium and 0-5% copper may be similarly treated. Such pasty mixtures are readily fabricated into pellets which are used on their own or which may be used as weights or parts of weights provided to weight boluses made from lighter materials.

A particularly useful pellet may alternatively be made by casting or extruding a hollow tubular body using a magnesium-based alloy containing 12% aluminium, and 2% copper, the body having a central cavity of which the volume is approximately 30% of the total volume of the pellet and is filled with a pasty mixture consisting of 1 part by weight of magnesium alloy according to the invention containing 38% zinc, 11% aluminium and 2% copper, the alloy being mixed with 3 parts by weight of S170 grade iron shot. The average density of such a pellet is approximately 2.8 gm/ml.

BRIEF DESCRIPTION OF THE DRAWINGS

The invention will be described further, by way of example, with reference to the accompany drawings, in which:

FIG. 4 is a sectional elevation illustrating another basic embodiment of pellet which is made of an alloy conforming to the invention, in this instance by compressing from alloy powder;

FIG. 5 is a diagrammatic sectional elevation illustrating an embodiment of bolus made from sections each formed of the alloy of the invention and adapted for the pulsed release of therapeutic and/or other active agents (not shown); and FIG. 6 is a view comparable with FIG. 5, but illustrating a modification.

DETAILED DESCRIPTION OF THE PREFERRED EMBODIMENTS

Figure 1:
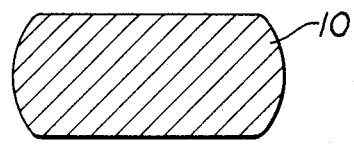
FIG. 1 is sectional elevation illustrating a basic embodiment of a pellet made of an alloy conforming to the present invention and consisting simply of the cast alloy.

Referring firstly to FIG. 1 of the drawings, this figure illustrates a simple embodiment of pellet, in the form of a cylindrical body or bolus 10 whose axial length is about twice to three times the diameter of the body, which is suitable for administration to a ruminant for therapeutic, growth-promoting or like purposes and which is made of an alloy conforming to the invention. The bolus 10 is composed primarily of a magnesium-zinc-aluminium-copper alloy in which the proportions of the individual components present in the alloy lie in the following ranges:

Magnesium: at least 40%
Zinc: at least 30%
Aluminium: at least 5%
Copper: 0 to 5%

After formation of the alloy, which is achieved by use of conventional melting techniques, and which has a relatively low melting point, it is simply cast by being poured into an appropriate mould or die (not shown). As will be understood, this body or bolus 10, upon administration to an animal such as a cow or sheep, is progressively eroded away by the rumen juices thereby to provide for continuous release of the components of the alloy into the animal's rumen. The magnesium is, of course, effective to combat hypomagnesaemia, and the copper is effective to eliminate copper deficiency.

The following illustrates a typical example of a specific alloy suitable the production of a pellet or bolus for administration to ruminants:

Magnesium: 50%
Zinc: 40%
Aluminium: 8%
Copper: 2%

In position in the rumen, the bolus 1 is gradually eroded and/or dissolved by the rumen fluids, thereby continuously releasing the alloy constituents for assimilation by the treated animal. As mentioned, the bolus serves primarily to administer magnesium to the animal's system to combat hypomagnesaemia.

Practical experiments show that a pellet or bolus according to the formulation just described will erode at a rate to deliver approximately 50% of its weight to an animal in a period of 10 to 14 days. Obviously, however, the rate of erosion and delivery of the constituents will depend upon the precise percentages of the various constituents in the alloy. Erosion and/or dissolution (and consequently active agent delivery) is found to be particularly influenced by the aluminium and copper content of the alloy, as will readily be appreciated from the dissolution rates observed in the testing of series of boluses according to FIG. 1 in cattle and using different alloys within the scope of the invention as indicated in the following table:

| Alloy of bolus | Period for 50% weight loss |
| --- | --- |
| Mg 50%; Zn 37%; Al 8%; Cu 5% | 5 to 7 days |
| Mg 50%; Zn 40%; Al 8%; Cu 2% | 10 to 13 days |
| Mg 48%; Zn 38%; Al 12%; Cu 2% | 28 to 36 days |

In its most elementary form, therefore, the pellet or bolus of the invention may comprise simply the magnesium-based alloy as above defined, without additives, in which case the alloy, upon erosion in the animals stomach will essentially serve to supply magnesium to the treated animal for combatting magnesium deficiency. Where copper is present in the alloy, this element will be released and will serve to alleviate copper deficiency, and so forth. The alloy may simply comprise the alloy in its initially prepared form, simply produced by melting and casting of its components.

As an alternative to casting the alloy as just described, the alloy can be heated to a temperature between its solidus and liquidus temperature and mixed with iron particles to bring the mixture to a plastic condition which can be shaped to a desired bolus or pellet shape, or can be incorporated into such a bolus or pellet.

Figure 2:
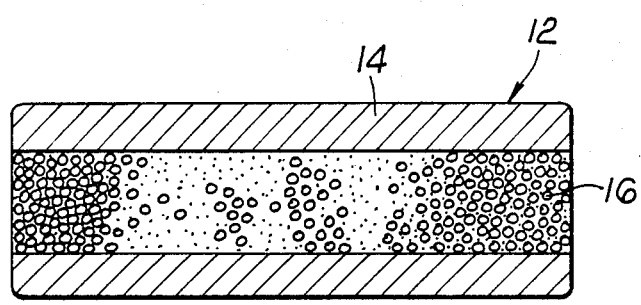
FIG. 2 is a sectional side elevation illustrating a second embodiment of pellet which in this instance comprises a cast hollow body incorporating a filling including an alloy conforming to the invention in combination with weighting material.

Turning now to FIG. 2 of the drawings, this figure illustrates a simple development from the pellet or bolus of FIG. 1. In this embodiment, the bolus or pellet, indicated generally by the reference numeral 12 comprises a tubular outer sheath or body 14 which is open at its ends (but may be open at one end only) and contains a filling 16, this filling 16 containing magnesium-based alloy conforming to the invention, containing zinc, aluminium and copper in the ranges as discussed above, as at least part thereof.

More particularly, for example, the outer sheath or body 14 itself may itself comprise a cast magnesium-based alloy conforming to the invention, but preferably it contains magnesium in the range 83 to 90%, aluminium 8 to 17%, and copper 0 to 2%. A typical alloy for the sheath or body 14 comprises:

Magnesium: 86%
Aluminum: 12%
Copper: 2% and the sheath or body 14 may be produced by casting (e.g., gravity diecasting or pressure diecasting) or by extrusion without the need for any special precautions or techniques other than those which are customary with magnesium working. In the illustrated case, the interior cavity within the sheath or body 14, and occupied by the filling 16, has a volume approximating to 30% of the total volume of the bolus or pellet 12. The dimensions of the sheath or body 14 may, however, be such as to provide for the cavity to represent a different proportion of the total volume, for example in the range from 5 to 50% of such volume, Turning now to the filling 16, which comprises the magnesium/zinc based alloy conforming to the invention, this filling 16 is produced as follows. Firstly, the magnesium alloy is prepared, using conventional melting techniques, typically with a composition comprising:

Magnesium: 45 to 50%—preferably 49%
Zinc: 30 to 40%—preferably 38%
Aluminum: 5 to 15%—preferably 11%
Copper: 0 to 5%—preferably 2%

The alloy is brought to a temperature between its solidus and liquidus temperatures and is maintained thereat whilst it is mixed with iron shot; for instance S170 grade, in the ratio of 3 parts by weight of the iron shot to one part weight of the magnesium-based alloy. This has the effect of producing a pasty mixture of higher density than that of the alloy alone, for instance of the order of 5 gm/ml. The low melting point and low tendency of the molten alloy to oxidation enable the mixing to be effected easily to achieve the pasty composition which is itself readily worked to form the filling 16. Introduction of the filling 16 into the sheath or body 14 is effected, for example, simply by filling the alloy/iron shot paste, at an appropriate temperature to keep it in a pasty condition between the solidus and liquidus temperature of the alloy, into the interior of the body or sheath 14.

The resultant bolus, wherein the internal cavity, occupied by the filling 16, is about 30% of the volume of the whole, has a density of about 2.8 gm/ml and can, of course, be administered to a ruminant in the same way and for the same purposes as above described for FIG. 1. Naturally, it may incorporate other additives, such as excipients, strength-improving agents, galvanic-reaction promoting materials and trace elements, such as cobalt and selenium.

In use of the bolus or pellet of FIG. 2, the treated animal's rumen fluids are able to act on the exterior body 14 which tends to dissolve preferentially to the core or filling 16. The density of the bolus or pellet hence tends to increase with time, aiding retention by the animal. When the body 14 has dissolved, the core or filling 16, which has hitherto been eroded only from its ends, tends to disintegrate, liberating the magnesium and other ingredients.

Figure 3:
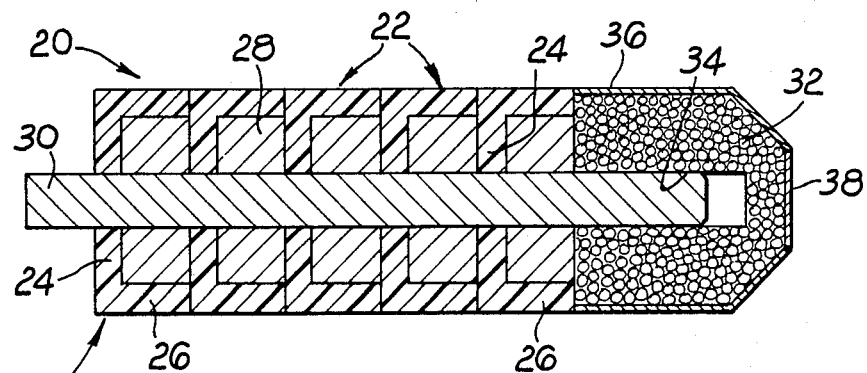
FIG. 3 is a sectional side elevation illustrating a bolus for use in adminstering therapeutic or other active materials, to a ruminant, which bolus incorporates a mass, consisting of the alloy of the invention incorporating weighting material, as an endweight of the bolus.

Turning now to FIG. 3 of the drawings, this figure illustrates how the alloy of the invention, admixed with iron or other heavy metal shot, may be used as an endweight of a bolus for the administration of therapeutic agents and/or other active materials to animals, of the kind described in detail in the specification of prior co-pending European Application for Patent No. 85 30 34 61.9 (Publication No., 01 64 927). Such boluses are all constructed to deliver doses of active materials at spaced intervals of time, and it is desirable that after release of the final dose the endweight should be eliminated or degraded to such an extent that neither the well-being nor the final processing of the animal are prejudiced. The use of the alloy/shot mixture in or as the endweight serves to contribute toward this. Although FIG. 3 illustrates only one such bolus, it will readily be understood that the alloy of the present invention may be used in connection with the endweights of each of the boluses of the said prior co-pending patent application of the kind incorporating an endweight.

Referring now to FIG. 3 in more detail, the bolus, indicated generally by numeral 20, comprises a plurality of pocket elements 22 e.g., of a substantially inert plastics material, each of which elements 22 comprises a basic disc 24 having a flange in the form of a projecting sleeve 26 which is relatively short axial length and defines a respective pocket for reception of a respective filling 28 which is of or contains an active material having an anthelmintic, bactericidal, fungicidal or other activity all as described in detail in the above-mentioned co-pending application.

If desired the material used for the pocket elements 22 may be a magnesium alloy or other degradable material. Each filling 28 may, of course, be in the form of a compressed tablet, and as can be seen the pocket elements 22 are a tight fit upon a central rod 30, e.g., of magnesium alloy, and each sleeve 26 is effectively externally sealed relative to its neighbouring pocket element by pressing firmly thereagainst.

As mentioned, the pocket elements 22 are located relative to one another by being a tight fit on the central magnesium rod 30, the fillings 28 accordingly being annular tablets. Release of the first of such fillings or doses 30 only occurs, of course, when the rod 30 has been sufficiently eroded away to allow the first pocket element (indicated at A) to fall away and such filling 28 to become exposed to the rumen juices. This dosing operation of the bolus is repeated each time the rod 30 erodes away sufficiently to release a further one of the elements 22.

At the end of the bolus, remote from the first pocket element A, the rod 30 engages with an endweight 32, which is a tight push fit on the rod 30 and is in the form of a shaped body which is moulded from a pasty mixture produced in the same way as the fillings 16 of FIG. 2, or, for example, by packing a suitably shaped mould with a maximum of iron shot, such as B.S.S. iron shot grade S170 or S110, and bonding the shot particles with magnesium/zinc/aluminum/copper alloy conforming to the invention (the constituents thereof being present in the proportions above discussed and preferably with Magnesium-50%, Zinc-40%, Aluminium-8%, Copper-2%). The alloy occupies substantially all of the interstices between the shot particles. This gives an endweight 32 with a specific gravity in excess of 5 gm/ml, for instance of the order of 5.5 gm/ml. The resultant body may, after moulding, be appropriately machined to any suitable shape, including, for instance, the necessary bore 34 for engaging on the rod 32, and is backed off preferably to a rounded configuration at the remote end thereof.

In this embodiment, the endweight 32 is externally coated with an inert material 36 except at an exposed disc 38, e.g., of iron, which is exposed to rumen fluids and contributes to controlling degradation or erosion of the rod 30 by reason of the galvanic couple set up therebetween. When all of the doses 28 have been released, the material of the endweight will be fully exposed to rumen juices for erosion, and will disintegrate and liberate magnesium in the same way as the filling 16 of the embodiment of FIG. 2.

In the embodiment of FIG. 3, the central rod 30 can be omitted and the adjacent pocket elements 22 may then be designed to be erodible and a push fit into one another, with the endweight 32 correspondingly being an interference fit with its respective endmost one of the pocket elements 22. In this case, the rate of release of the doses of the fillings 28 will depend solely upon the rate of degradation and erosion of the pocket elements 22. In the illustrated case, where the central rod 30, which may for example be of aluminium, of magnesium alloy or magnesium, or any other suitable erodible metal or alloy, is present, the rate of erosion of this rod will contribute to controlling the speed of release of the fillings 28, and where a galvanic action is set up between the material of the rod 30 and means such as the disc 38, such galvanic action will, of course, be relevant to the rate of dosage.

Referring now to FIG. 4 of the drawings, this figure illustrates diagrammatically a bolus or pellet 60 made of the alloy of the invention but which is produced in a very different way from that of FIG. 1 and which has significant practical advantages over the FIG. 1 proposal.

In this instance, one starts once again with the basic alloy materials, namely magnesium, zinc, aluminium and copper, in the proportions as discussed in the foregoing and subjects these to melting treatment to form the requisite molten alloy which is cast in any suitable shape and is allowed to cool and solidify. The solid alloy is then converted into particulate or powder form by mechanical treatment, for instance by ball milling, grinding, scratching or in any other suitable way.

To make the bolus or pellet of FIG. 4, an appropriate quantity of the powdered alloy is simply filled into a pellet mould and is compressed, e.g., by use of a hydraulic press, using sufficient pressure to convert the powder into a coherent mass of the desired shape, such as is illustrated, suitable for administration to a ruminant. This bolus or pellet 60 can be used in precisely the same manner as those of the preceding examples, particularly that of FIG. 1.

It will readily be perceived, however, that this manner of creating the bolus or pellet 60 opens up the possibility of including into the device a wide range of additives in order to obtain the benefit of their respective properties, especially additives which could not be incorporated into the cast alloy of the device of FIG. 1 by reason of being adversely affected by the elevated temperatures necessary for the casting of the alloy. Thus, in this case, apart from the possibility of incorporating excipients, additives which facilitate the compression of the powder and/or contribute to the coherence of the eventual product, high melting point trace elements and other active agents, it is possible to incorporate, e.g., in powder or other suitable form, active ingredients dense elements, such as iron and zinc powders to increase density, nutrients, therapeutic agents, e.g., vitamins, anthelmintics, growth promoters, trace elements and the like which would be or might be adversely affected at elevated temperatures. Moreover, use could, if desired, be made of binder, such as methacrylate resin, for binding the alloy particles, such resin being degradable within the dosed animal's rumen, and thereby providing for time delay in administration if desired.

In making a typical example, 5 gm of growth promoter was mixed with 10 gm of a powdered alloy containing 50% Mg, 40% Zn, 8% Al, 2% Cu, together with 31 gm iron powder, 11 gm zinc powder and 1 gm zinc stearate power. The mixed powders were compressed in a 25 mm diameter tubular die under a pressure of 30 tonnes. The resultant compact had a density of 5.1 gm/ml. Such pellets dissolve slowly over a period of several weeks or months in a cow's rumen. The rate of dissolution may be controlled by varying the amounts of the various constituent powders in the compact and the composition of the Mf-Zn-Al-Cu alloy. Pellets may be vacuum impregnated with resin or other sealants to reduce internal porosity and improve their performance.

FIG. 5 illustrates an embodiment of bolus comprising a succession of cup-like pocket elements 62 each of which is produced in an analogous manner to the pellet of FIG. 4 but without necessarily incorporating active ingredients, but preferably incorporating weighting material so as to exceed a density of 2.2 gm/ml. In this case, each pocket element 62 is of a configuration, externally of its base, such as to provide a surrounding recess 64 into which the rim of an identical pocket element 62 will fit. This enables the elements 62 to be assembled in a stack in the manner shown with the rim of each pocket element locates into the recess 64 of the next adjacent element 62, except at the endmost element 62 whose rim locates into a circumferential recess 66 in a closure plate 68. As will readily be understood from FIG. 5, each element 62 provides a respective cavity or pocket 70 for accommodating a respective filling (not shown) of active material, e.g., in the form of a compressed tablet, paste, liquid, or as desired, and each such filling will be released as a respective pulsed dose when its element 62 or the next adjacent such element, has been eroded away. The pocket elements 62 and the closure plate 68 are sealed in place relative to one another by use of hardening synthetic resin or other adhesive therebetween, and such resin may, if desired, be provided around each of the pocket elements 62 to protect them against attack by rumen juices, so that erosion proceeds only from the closure plate end. Of course, the exterior of the bolus may be sheathed or sealed against degradation by environmental fluids by any suitable material and this may be present over part or substantially the whole of the external surface of the bolus (except that part thereof whereat erosion is specifically required). If desired, this bolus may be constructed so as to enable it to incorporate an endweight comparable with that of the embodiment of FIG. 3.

The embodiment of bolus illustrated in FIG. 6 is largely similar to that of FIG. 5, and similar reference numerals have been allocated to similar parts. In this embodiment, instead of relying upon the pocket elements 62 being adhered to one another, and the closure plate 68 correspondingly being adhered in place, using acrylic resin, these components are located in place by being an interference fit on or being screw-threaded upon a central rod 72 which is similar in its form and effect to the rod 32 in the embodiment of FIG. 3.

Of course, in the embodiments of FIGS. 4 to 6, each pellet or bolus may, if desired, be provided with a respective endweight similar to the endweight 32 in the embodiment of FIG. 3. If desired, of course, the elements 62, 68 of the embodiments of FIGS. 5 and 6 may be made by casting in a manner analagous with what has been described above with reference to FIGS. 1 to 3. Other variations are possible.

As has already been mentioned, the percentages above recited are all by weight. The same applies to the percentages given in the following claims.

What is claimed is:

1. An alloy of which the constituents, or the principal constituents, are magnesium, zinc and aluminium, and suitable for use in the production of, or incorporation in, a pellet for administration to a ruminant by deposition in its rumeno-reticular sac, characterised in that said alloy comprises magnesium to the extent of at least 40%, zinc at least 30% and aluminium up to 20% by weight.

2. An alloy as claimed in claim 1 further including copper in an amount of up to 5%.

3. An alloy as claimed in claim 1 or 2 characterised in that it comprises:
   magnesium—from 45% to 50%
   zinc—from 34% to 42%
   aluminium—from 5% to 15%
   copper—from 0 to 5%.

4. An alloy as claimed in claim 3 characterised in that it comprises:
   magnesium—50%
   zinc—40%
   aluminium—8%
   copper—2%
or:
   magnesium—50%
   zinc—37%
   aluminium—8%
   copper—5%
or:
   magnesium—48%
   zinc—38%
   aluminium—12%
   copper—2%.

5. An alloy as claimed in any preceding claim further including one or more additional elements selected from cobalt, manganese, nickel, iron and selenium, in amounts up to 1% each.

6. A mixture, suitable for fabrication into a pellet for administration to a ruminant by deposition in its rumeno-reticular sac, comprising an alloy as claimed in any preceding claim incorporating iron shot.

7. A mixture as claimed in claim 6 characterised in that it comprises three parts by weight of iron shot and one part by weight of the alloy.

8. A mixture as claimed in claim 6 or 7 wherein the alloy comprises about 38% zinc, 11% aluminium, and 2% copper.

9. A method of making a pellet for administration to a ruminant by deposition in its rumeno-retircular sac which comprises converting an alloy as claimed in any preceding claim to particulate form, filling the same into a mould or die, and compressing the same to form a pellet.

10. A method as claimed in claim 9 wherein iron powder and additional zinc powder are mixed with the particulate alloy before compressing.

11. A method as claimed in claim 10 wherein the alloy, and the added iron and zinc powders are present in the amounts of:
    alloy—10 parts by weight
    iron powder—31 parts by weight
    zinc powder—11 parts by weight.

12. A pellet for administration to a ruminant by deposition in its rumeno-reticular sac, characterised in that it comprises an alloy as claimed in any of claims 1 to 7.

13. A pellet as claimed in claim 12 wherein the pellet is a coherent body comprising compressed particles of the alloy.

14. A pellet as claimed in claim 12 and which comprises an outer sheath and an inner filling.

15. A pellet as claimed in any of claims 12 to 14 which further comprises an endweight which incorporates the alloy.

16. A pellet as claimed in claim 14 wherein the filling comprises the alloy.

17. A pellet as claimed in claim 12 wherein the pellet comprises a plurality of pocket elements each accommodating a respective filling.

18. A pellet as claimed in claim 17 wherein each said pocket element is made of the alloy.

19. A pellet as claimed in any of claims 12 to 18 which comprises an endweight which incorporates the alloy.

20. An alloy of which the constitutents, or the principal constitutents, are magnesium, zinc and aluminum, and suitable for use in the production of, or incorporation in, a pellet for administration to a ruminant by deposition in its rumeno-reticular sac, characterized in that said alloy comprises magnesium to the extent of at least 40%, zinc at least 30% and wherein the aluminum content is greater than zero and up to 20% by weight.

21. An alloy of which the constitutents, or the principal constitutents, are magnesium, zinc and aluminum, and suitable for use in the production of, or incorporation in, a pellet for administration to a ruminant by deposition in its rumeno-reticular sac, characterized in that said alloy comprises magnesium to the extent of at least 40%, zinc at least 30% and wherein aluminum content is from 5 to 20% by weight.

* * * * *